(12) United States Patent
Mach

(10) Patent No.: US 9,814,682 B2
(45) Date of Patent: Nov. 14, 2017

(54) VACCINATION WITH IMMUNO-ISOLATED CELLS PRODUCING AN IMMUNOMODULATOR

(71) Applicant: Maxivax SA, Geneva (CH)

(72) Inventor: Nicolas Mach, Collonge-Bellerive (CH)

(73) Assignee: MaxiVax SA, Geneva (CH)

(*) Notice: Subject to any disclaimer, the term of this patent is extended or adjusted under 35 U.S.C. 154(b) by 394 days.

(21) Appl. No.: 14/218,171

(22) Filed: Mar. 18, 2014

(65) Prior Publication Data

US 2014/0341982 A1    Nov. 20, 2014

Related U.S. Application Data

(63) Continuation of application No. 11/900,670, filed on Sep. 12, 2007, now abandoned, which is a (Continued)

(30) Foreign Application Priority Data

Jun. 17, 2002   (EP) ..................... 02013249

(51) Int. Cl.
*A61K 9/00* (2006.01)
*A61K 38/00* (2006.01)
(Continued)

(52) U.S. Cl.
CPC .............. *A61K 9/48* (2013.01); *A61K 38/18* (2013.01); *A61K 38/193* (2013.01);
(Continued)

(58) Field of Classification Search
CPC ........ A61K 9/48; A61K 38/18; A61K 38/193; A61K 39/0011; A61K 39/21; A61K 39/29; A61K 39/39; C12N 11/04; C12N 15/85
See application file for complete search history.

(56) References Cited

U.S. PATENT DOCUMENTS

| 4,680,174 A | 7/1987 | Javis, Jr. et al. |
| 5,637,483 A | 6/1997 | Dranoff et al. |

(Continued)

FOREIGN PATENT DOCUMENTS

| EP | 1 159 967 | 12/2001 |
| WO | WO 98/16246 | 4/1998 |

(Continued)

OTHER PUBLICATIONS

Borrello et al., (Human Gene Therapy. Aug. 10, 1999;10:1983-1991).*

(Continued)

*Primary Examiner* — Cherie M Stanfield
(74) *Attorney, Agent, or Firm* — Cooley LLP; Ivor R. Elrifi; Christina K. Stock

(57) ABSTRACT

The present invention relates to immuno-protected encapsulated cells producing an immunomodulator, for example GM-CSF (granulocyte-macrophage colony stimulating factor). The cells of the invention are particularly well adapted for providing an active adjuvant or immunomodulator, for example in the context of immunization in humans and animals. These cells can be used for vaccination where they provide the immunomodulator in an active form, in a continuous, non-immunogenic manner in the immediate vicinity of the vaccine antigen(s). The invention also relates to a vaccine composition comprising immuno-protected encapsulated cells producing an immunomodulator and an antigenic component. The invention also relates to a kit comprising a cell as described and an antigenic component. The strategy of the invention is perfectly suited for both cancer immunotherapy and vaccination against infectious agents.

17 Claims, 5 Drawing Sheets

Related U.S. Application Data continuation of application No. 11/058,883, filed on Feb. 16, 2005, now abandoned, which is a continuation of application No. 10/464,565, filed on Jun. 17, 2003, now abandoned.

(51) Int. Cl.
| | |
|---|---|
| *C12N 7/00* | (2006.01) |
| *A61K 9/48* | (2006.01) |
| *A61K 38/19* | (2006.01) |
| *A61K 39/00* | (2006.01) |
| *A61K 39/39* | (2006.01) |
| *A61K 38/18* | (2006.01) |
| *A61K 39/21* | (2006.01) |
| *A61K 39/29* | (2006.01) |
| *C12N 11/04* | (2006.01) |
| *C12N 15/85* | (2006.01) |

(52) U.S. Cl.
CPC .......... *A61K 39/0011* (2013.01); *A61K 39/21* (2013.01); *A61K 39/29* (2013.01); *A61K 39/39* (2013.01); *C12N 7/00* (2013.01); *C12N 11/04* (2013.01); *C12N 15/85* (2013.01); *A61K 2039/5152* (2013.01); *A61K 2039/55522* (2013.01); *C12N 2740/16011* (2013.01); *C12N 2770/24211* (2013.01)

(56) References Cited

U.S. PATENT DOCUMENTS

| | | | |
|---|---|---|---|
| 5,679,356 A | 10/1997 | Bonnem et al. | |
| 5,861,159 A | 1/1999 | Pardoll et al. | |
| 5,904,920 A * | 5/1999 | Dranoff ................. | A61K 39/12 424/93.21 |
| 5,955,095 A * | 9/1999 | Gentile ................ | A61K 9/4816 424/422 |
| 6,193,970 B1 | 2/2001 | Pardoll et al. | |
| 6,916,640 B2 | 7/2005 | Yu et al. | |
| 7,250,291 B1 | 7/2007 | Dranoff et al. | |
| 2005/0118425 A1 * | 6/2005 | Childs ................. | A61K 9/0024 428/402.2 |

FOREIGN PATENT DOCUMENTS

| | | |
|---|---|---|
| WO | WO 98/33520 | 8/1998 |
| WO | WO 99/38954 | 8/1999 |
| WO | WO 02/080972 | 10/2002 |

OTHER PUBLICATIONS

Schwenter et al., (Cancer Gene Therapy. 2011;18:553-562).*
Abaza et al., "Effects of amino acid substitutions outside an antigenic site on protein binding to monoclonal antibodies of predetermined specificity obtained by peptide immunization: demonstration with region 94-100 (antigenic site 3) of myoglobin", J. Protein Chem. 11(5): 433-44 (1992).
Aruga et al., "Cancer Research", Aug. 1, 1997; 57; 3230-3237.
Bar et al., "Inhibition of tumor growth by the continuous delivery of IL-1 receptor antagonist (IL-1Ra) from microencapsulated genetically-engineered cells", J. Controlled Release, 72:228-229 (2001).
Bessis et al., "Encapsulation in hollow fibres of xenogeneic cells engineered to secrete IL-4 or IL-13 ameliorates murine collagen-induced arthritis (CIA)", Clin. Exp. Immunol., 177:376-382 (1999).
Billington, W.D., "Maternal immune response to pregnancy", Reprod. Fertil. Dev., 1(3):183-190 (1989).
Bonazzi et al., "Bacterial entry into cells: a role for the endocytic machinery", FEBS Lett., 580(12):2962-2967 (2006).
Borello et al., "Human Gene Therapy", Aug. 10, 1999; 10:1983-1991.
Cirone et al., "Immuno-isolation in oncology—a mini-review", Curr. Pharm. Biotechnol., 2:269-277 (2001).
Cohen et al., "Pronounced acute immunosuppression in Vivo mediated by HIV Tat challenge", Proc. Natl. Acad. Sci. USA, 96:10842-10847 (1999).
Cotran et al., in Pathologic Basis of Disease, Sixth Edition, pp. 311-314 (1999).
Crystal, R.G., "Transfer of genes to humans: early lessons and obstacles to success", Science, 270:404-410 (1995).
Danos et al., "Safe and efficient generation of recombinant retroviruses with amphotropic and ecotropic host ranges", Proc. Natl. Acad. Sci. USA, 85:6460-6464 (1988).
Database BIOSIS 'Online', Biosciences Information Service, Philadelphia, PA, US; Nov. 16, 2000, McNall Rene et al., "Tumor vaccines with cytokine secreting bystander cells in murine AML", Database accession No. PREV200100299398 (Abstract) & Blood, 42$^{nd}$ Annual Meeting of the American Society of Hematology, San Francisco, CA, 96(11):122a (2000).
Dranoff et al., "Vaccination with irradiated tumor cells engineered to secrete murine granulocyte-macrophage colony-stimulating factor stimulates potent, specific, and long-lasting anti-tumor immunity", Proc. Natl. Acad. Sci. USA, 90:3539-3543 (1993).
Fox, J.L., "No winners against AIDS", Biotechnol., 12:128 (1994).
Gura, T., "Systems for identifying new drugs are often faulty", Science, 278:1041-14042 (1997).
Illustrated Dictionary of Immunology, CRC Press, Inc., Vaccine (1995).
Jaffee et al., "High efficiency gene transfer into primary human tumor explants without cell selection", Cancer Res., 53:2221-2226 (1993).
Jaffee et al., "Novel allogeneic granulocyte-macrophage colony-stimulating factor-secreting tumor vaccine for pancreatic cancer: a phase I trial of safety and immune activation", J. Clin. Oncol., 19(1):145-156 (2001).
LaTemple et al., "Increased Immunogenicity of tumor vaccines complexed with anti-gal: studies in knockout mice for α1,3Galactosyltransferase", Cancer Res., 59:3417-3423 (1999).
Lu et al., "Pregnancy as a natural model of allograft tolerance. Interactions between adherent macrophages and trophoblast populations", Transplantation, 48(5):848-855 (1989).
Mach et al., "Cancer Research", Jun. 15, 2000, 60; 3239-3246.
Mach et al., "Curr Opin Immunol", Oct. 2000; 12(5):571-5. Review.
McNall et al. "Tumor Vaccine With Cytokine Secreting Bystander Cells in Murine AML." Blood. 96.11Part1(2000):122a. (Abstract Only).
Ory et al., "A stable human-derived packaging cell line for production of high titer retrovirus/vesicular stomatitis virus G pseudotypes", Proc. Natl. Acad. Sci. USA, 93:11400-11406 (1996).
Paul, W.E., Fundamental Immunology, Raven Press, Ltd., pp. 1311-1312 (1993).
Riffkin et al., "A single amino-acid change between the antigenically different extracellular serine proteases V2 and B2 from Dichelobacter nodosus", Gene, 167:279-283 (1995).
Schilbach et al., "Human γδ T lymphocytes exert natural and IL__2-induced cytotoxicity to neuroblastoma cells", J. Immunother., 23:536-548 (2000).
Shao et al., "Delivery of cytokines by microencapsulated transduced cells", Proceed. Intern. Symp. Control. Rel. Bioact. Mater., 21:46-47 (1994).
Shehu-Xhilaga et al., "Antiretroviral compounds: mechanisms underlying failure of HAART to eradicate HIV-1", Curr. Med. Chem., 12(15):1705-1719 (2005).
Simons et al., "Induction of immunity to prostate cancer antigens: results of a clinical trial of vaccination with irradiated autologous prostate tumor cells engineered to secrete granulocyte-macrophage colony-stimulating factor using ex vivo gene transfer", Cancer Res., 59(20):5160-5168 (1999).
Simons et al., "Bioactivity of human GM-CSF gene therapy in metastatic renal cell carcinoma and prostate cancer", Acta Urol. Jpn., 43(11):821-822 (1997).
Soiffer et al., "Vaccination with irradiated autologous melanoma cells engineered to secrete human granulocyte-macrophage colony-

(56) References Cited

OTHER PUBLICATIONS stimulating factor generates potent antitumor immunity in patients with metastatic melanoma", *Proc. Natl. Acad. Sci. USA*, 95:13141-13146 (1998).

Tait et al., "Ovarian cancer BRCA1 gene therapy: phase I and II trial differences in immune response and vector stability", *Clin. Cancer Res.*, 5:1708-1714 (1999).

Teshima et al. Cancer Research, Jan. 1, 2001; 61:162-171.

Von Mehren et al., "The influence of granulocyte macrophage colony-stimulating factor and prior chemotherapy on the immunological response to a vaccine (ALVAC-CEA B7.1) in patients with metastatic carcinoma", *Clin. Cancer Res.*, 7(5):1181-1191 (2001).

Weinberg et al., "Are viral-encoded microRNAs mediating latent HIV-1 infection?", *DNA Cell Biol.*, 25(4):223-231 (2006).

\* cited by examiner

|   | Day 4 | Day 7 | Day 11 | Day 14 | Day 21 | mean | sem |
|---|---|---|---|---|---|---|---|
| 1 | 49 | 63.5 | 50.5 | 49 | - | 52.9 | 3.6 |
| 2 | 24.5 | 49.5 | 42 | 41 | - | 39.2 | 5.3 |
| 3 | 32.5 | 54 | 41.5 | 47.5 | - | 43.9 | 4.6 |
| 4 | 49 | 50.5 | 53 | 57.5 | 45 | 51 | 2.1 |
| 5 | 51 | 48 | 47.5 | 45.5 | 51 | 48.5 | 1.1 |
| 6 | 50 | 38 | 51.5 | 41 | 49.5 | 46 | 2.7 |
| 7 | 39.5 | 38 | 42.5 | 49 | 48.5 | 43.5 | 2.3 |
| 8 | 38 | 40 | 45.9 | 49 | 55 | 45.4 | 3.1 |
| 9 | 33 | 47.5 | - | - | - | 40.3 | 7.25 |
| 10 | 50.5 | 61 | - | - | - | 55.8 | 5.25 |
| mean | 41.7 | 49 | 46.62 | 47.37 | 49.8 | | |
| sem | 3 | 2.8 | 1.6 | 1.87 | 1.6 | | |

Figure 3

VACCINATION WITH IMMUNO-ISOLATED CELLS PRODUCING AN IMMUNOMODULATOR

RELATED APPLICATIONS

This application is a continuation of U.S. patent application Ser. No. 11/900,670, filed Sep. 12, 2007, which is a continuation of U.S. patent application Ser. No. 11/058,883, filed Feb. 16, 2005, which is a continuation of U.S. patent application Ser. No. 10/464,565, filed Jun. 17, 2003, which claims priority to European Patent Application No. 02013249.4, filed Jun. 17, 2002, each of which is incorporated herein by reference in its entirety.

FIELD OF THE INVENTION

The present invention relates to a new approach for providing an active adjuvant or immunomodulator, for example in the context of immunisation in humans and animals. According to this approach, an immunomodulator, for example GM-CSF (granulocyte-macrophage colony stimulating factor), is released from immuno-protected encapsulated cells producing this protein. This system is particularly well adapted to vaccination in that it provides the immunomodulator in an active form, in continuous, non-immunogenic manner in the immediate vicinity of the vaccine antigen(s). The strategy of the invention is perfectly suited for both cancer immunotherapy and vaccination against infectious agents.

BACKGROUND OF THE INVENTION

In the field of vaccination, first generation vaccines comprised only the antigen against which an immune response was desired. However, because the presence of an antigen alone is in most cases only weakly efficient, a second generation of vaccines was developed, wherein the vaccinating composition includes one or more adjuvants as immunomodulators to enhance this immune response.

Several different techniques have been reported for providing the adjuvant at the vaccination site, depending on the context of the immunisation.

In the context of antigen-based vaccines (as opposed to cell-based vaccines), a widely applicable technique used for providing the necessary adjuvant is simply to combine the antigen with the adjuvant in the vaccinating composition. The resulting composition is administered directly to the subject, thereby supplying the antigen and adjuvant in a simultaneous and co-localised manner.

This simple approach cannot however be used in all vaccination settings. For example, in most cancers, useful antigens are often not known. This is the case for most of the common cancers in human such as lung, colon, stomach, lymphoma, brain. Therefore, new immunisation strategies are needed such as a cell-based approach. Immunisation strategy involving cell-based vaccines, where the antigen(s) to which an immune response is required is (are) produced by whole cells implanted in a subject, necessitates the use of more elaborate techniques to ensure the efficient delivery of adjuvant.

One solution in this type of context is to directly inject the immunomodulator at the vaccination site. The immunomodulator may either be "naked", or alternatively may be administered in a slow release formulation using pegylated, liposomal microspheres (International patent application WO 98/33520, filed by Bystryn). This strategy is however limited by technical and biochemical difficulties, as well as some degree of systemic release inducing potential toxicities.

An alternative approach which has been proposed to circumvent the problems arising from the direct injection technique is the use of "by-stander cells" to locally produce the immunomodulators. According to this approach, cells producing the adjuvant are implanted in proximity to the source of the antigen, thereby providing an efficient local release of adjuvant at the vaccine site. The efficacy of this approach has been demonstrated in mice where the vaccine is a mix of GM-CSF secreting fibroblasts and irradiated tumour cells (Aruga et al, 1997, *Cancer Research*, 57, 3230-3237).

However, even this approach is not totally without drawbacks. Indeed, for human immunization, it is known that multiple immunizations are required. Since syngeneic by-stander cells are not easily available, allogenic cells are used in the vast majority of cases. Consequently, after the first injection, the "by-stander cells" are recognised by the immune system of the host (allorecognition) and are rejected, thereby preventing further production of immuno-modulator. In addition, the allorecognition of the "by-stander cells" jeopardizes the desired immune response against the antigenic substance of the vaccine.

In order to avoid this allorecognition, Borrello et al (Human Gene Therapy, 1999) has described a strategy in which the GM-CSF supplying cell is a cell line, K-562, which fails to express HLA class I or II antigens, potentially decreasing the magnitude of the alloresponses generated on repeated immunisations. The K-562 cells, engineered to secrete GM-CSF do not express MHC molecules on their surface. They are HLA negative. These cells are however human cancer cells and are highly sensitive to potent rejection mechanisms occurring without the involvement of HLA class I or II proteins. These defence strategies are less specific but very rapid and potent for cellular destruction. At least two subtypes of lymphocytes known as $\gamma\epsilon$ T cells or natural killer (NK) lymphocytes are known to attack and destroy foreign cells by mechanism independent of HLA class I or II. Regarding K-562 they are known to be very sensitive to NK cells and also to $\gamma\delta$ T cells (J. Immunotherapy 2000 23:536-548 Schilbach K. et al) and are therefore used as a positive control for NK cell activity.

It is therefore likely that K-562 by-stander cells injected at the vaccine site will be destroyed efficiently and quickly by non-MHC dependent cytotoxic mechanisms. This may very well significantly decrease the release of the immunomodulator.

Beside being very sensitive to rapid destruction by NK cells, K-562 cells can express MHC class I upon Interferon $\gamma$ exposure. It is possible that such cytokine could be present or released at the vaccination site during the first or after repeated immunizations. Such MHC class I upregulation will also lead to rapid cell destruction via classical cellular immunity.

For these reasons, use of cells such as K-562 in vaccination is associated with numerous drawbacks.

Another solution, widely used in the context of cell-based vaccines, for example in cancer therapy, is to couple the production of antigen and the release of immunomodulator, by engineering the cell which is the source of antigen, to also supply the immunomodulator. For example, in cancer vaccines, the source of antigen is usually a whole tumour cell. This cell can be engineered, for example by transfection, to simultaneously produce the necessary adjuvant. Potent, specific and long lasting anti-tumour immune responses have been reported in the mouse model using this technique, relying on retroviral vectors as the gene transfer method for engineering tumour cells delivering GM-CSF.

In view of the favourable results obtained in the mouse model, the initial human trials used the same strategy (Simons J W. et al. 1997 *Cancer Research*, 43(11); Soiffer R. et al. 1998, *Proc. Natl. Acad. Sci. USA*, 95, 13141; Simons et al. 1999, *Cancer Research*, 59(20)). However, the technique proved to be very labour intensive and time consuming, because the patient's cells, harvested surgically need to be expanded in vitro, for retroviral infection, preventing a wide use of the method.

The use of other viral vector for infecting the tumour cells has therefore been proposed to circumvent these difficulties. Engineered viruses like adenovirus can infect tumour cells very efficiently and with much simpler procedures. Because adenovirus can infect non-dividing cells, the harvested tumour cells can be infected right away, preventing the long and tedious primary culture step required when using retroviral vectors.

The major problem of the new viruses tested is that in most cases, some viral proteins will be expressed from the tumour cells after infection. These viral proteins are strongly recognized by the immune system as foreign, infectious agents. Therefore the initial goal of mounting an immune response against weak tumour antigens is skewed or diverted towards a viral protein. This results in masking the anti-tumour immune response. It also primes the recipient against subsequent immunization that will further increase the destruction of the injected cells. These two mechanisms will very likely decrease the efficacy of the anti-tumour immunization scheme.

Thus, whilst the use of autologous engineered tumour cells as combined source of antigen and adjuvant a priori minimizes the risk of undesirable immune response, the step of viral infection itself gives rise to significant problems.

In order to limit the problems arising from viral infection of autologous cells, new strategies have been developed which do not require patients' cells. According to these techniques, the antigenic source is provided by cell-lines derived from other patients with similar type of cancer. The patient is then immunized with repeated injections of irradiated, GM-CSF secreting, allogeneic (from another human being) tumour cells.

This strategy is based on the assumption that the cell-line used for the immunization shares some relevant antigens with the patient's own tumour and that these common antigens will allow the development of an immune response that will recognize the patient tumour cells and destroy them. A phase I clinical trial using such strategy has been published (Jaffee E. et al. 2001 *Journal of Clinical Oncology*, 19(1)).

However, the percentage of patients showing an immune response is much lower than in previous report using autologous cells secreting the same immunomodulator (GM-CSF) (Soiffer et al.).

To date, no technique has been reported which provides both a constant source of immunomodulator and an efficient immune response, whilst being substantially free of undesirable interactions with the natural or adaptative immune system.

SUMMARY OF THE INVENTION

The present invention provides a new approach overcoming the drawbacks associated with the previous strategies.

The invention is based on the immuno-isolation of adjuvant producing cells by a physical barrier such as a capsule.

The present invention provides a general protocol for vaccination, named "Maxi-Vax" characterized by the delivery, in close proximity, of antigens and of live cells engineered to secrete immuno-activating cytokines (such as GM-CSF), these cells being immuno-protected by macro- or micro-encapsulation in order to sustain prolonged in situ delivery of the immune activator.

A particular case of the invention utilises macro-encapsulation of cells in hollowfibers PES capsules, but other forms of encapsulation, within devices or within gel matrices, are included in the invention.

A particular case of the invention concerns the use of cancer cells as the antigen, for the purpose of immunising against cancer-specific antigens and establishing a systemic anti-tumour cell protective immune response. The later case is referred to as "Onco-Maxi-Vax".

Another particular case of the invention applies to vaccination against infectious agents, such as viruses (including HIV and Hepatitis C).

The vaccination treatment with Onco-Maxi-Vax comprises repeated immunizations. The immunization is repeated at two week intervals at different sites, always sub-cutaneous. The total number of vaccination is a minimum of five.

∇: surgery and cell harvesting and processing of patients own cells

Figure 1:
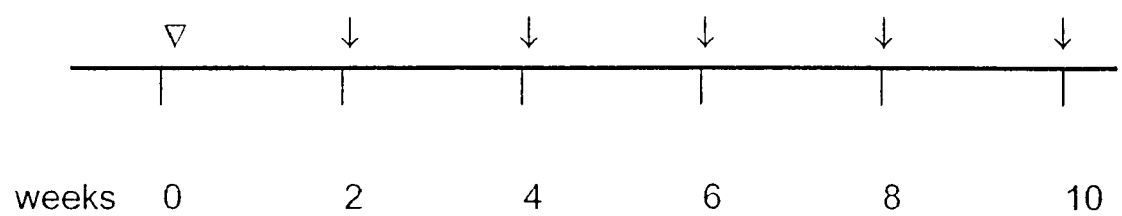
FIG. 1: Clinical immunization protocol for Onco-Maxi-Vax
Figure 2:
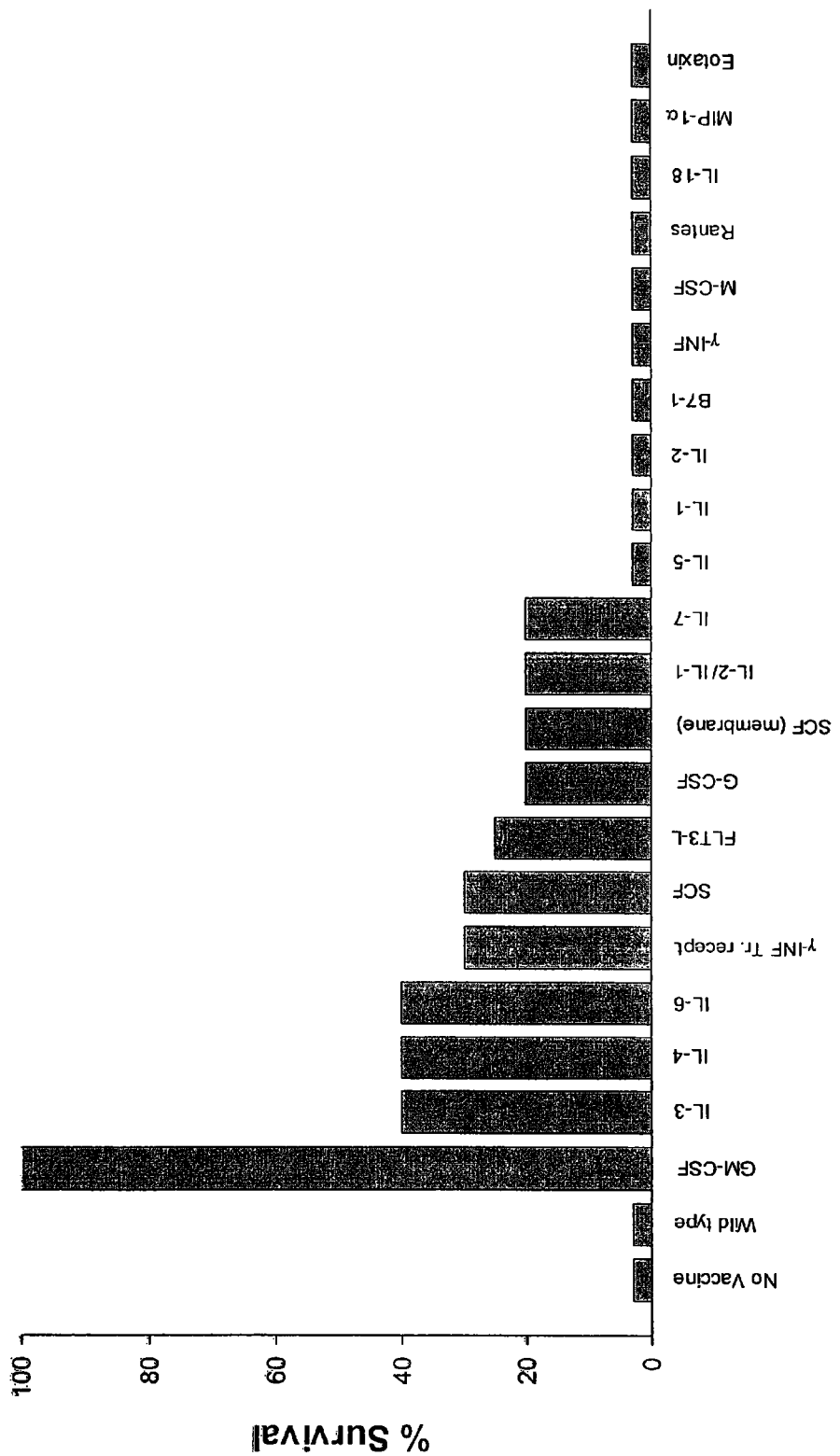

↓: Immunization with Onco-Maxi-Vax: encapsulated, irradiated GM-CSF producing cells and irradiated autologous tumour cells FIG. 2: Protective immunity against wild-type tumour challenged by various irradiated, cytokine secreting tumour cells.

This figure compares the efficacy of various immunomodulatory molecules in vaccination mouse model. Each block represents the percentage of mice surviving a tumour challenge after vaccination with irradiated tumour cells producing the described molecule.

All of the mice vaccinated with irradiated tumour cells secreting GM-CSF are protected. 25% of the mice vaccinated with irradiated tumour cells secreting FLT3-L are protected.

FIG. 3: GM-CSF release from encapsulated, non irradiated Renca-GM-CSF secreting cells.

This table shows an analysis of GM-CSF secretion outside the capsule at various time points by encapsulated, GM-CSF secreting Renca cells. GM-CSF release is expressed in ng/capsule/24 h.

Measurement of in-vitro release of murine GM-CSF from the capsule containing GM-CSF secreting cells is carried out at Days 4, 7, 11, 14 and 21 post loading the cells into the capsule. This is performed with standard monoclonal antibodies against murine GM-CSF in Enzyme-Linked immunoabsorbent Assays (ELISA). (R&D systems). The amounts of protein released as well as the reproducibility from one capsule to the others are assessed.

Figure 4:
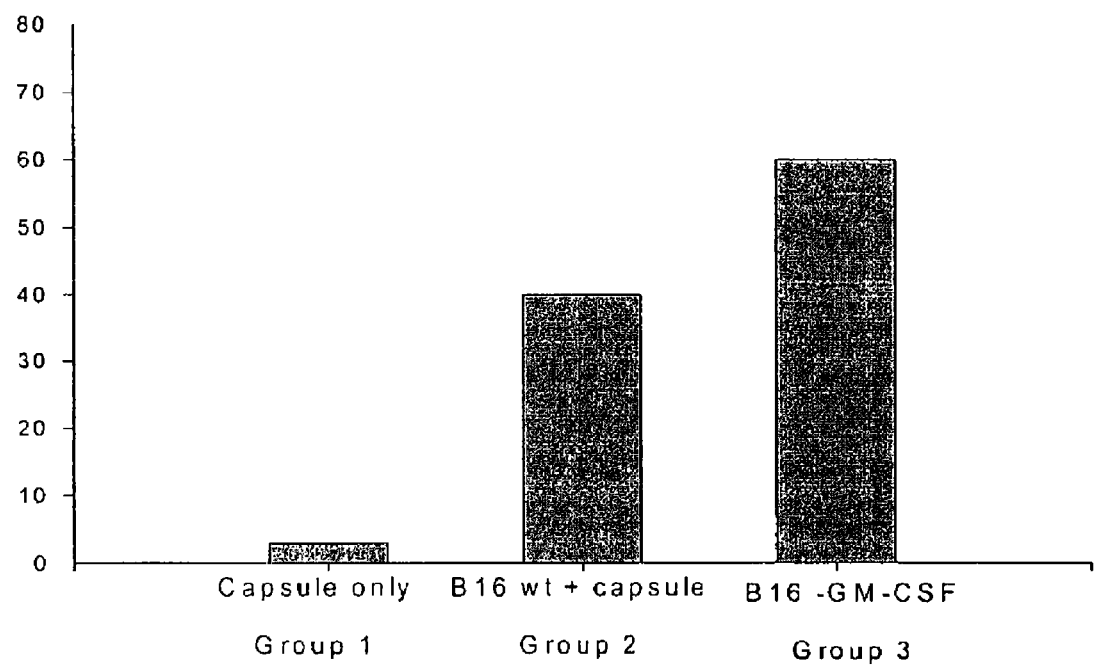

FIG. 4: Survival at 50 days after B16WT challenge.

This graph shows the survival at 50 days of mice immunized at day −7 with either irradiated, encapsulated GM-CSF secreting Renca cells only (group 1), either irradiated, encapsulated GM-CSF secreting Renca cells plus irradiated B16 wt melanoma cells (group 2); or irradiated, non-encapsulated B16 melanoma cells engineered to secrete GM-CSF (group 3);

The graph represents the mean value over 5 mice per group.

Figure 5:
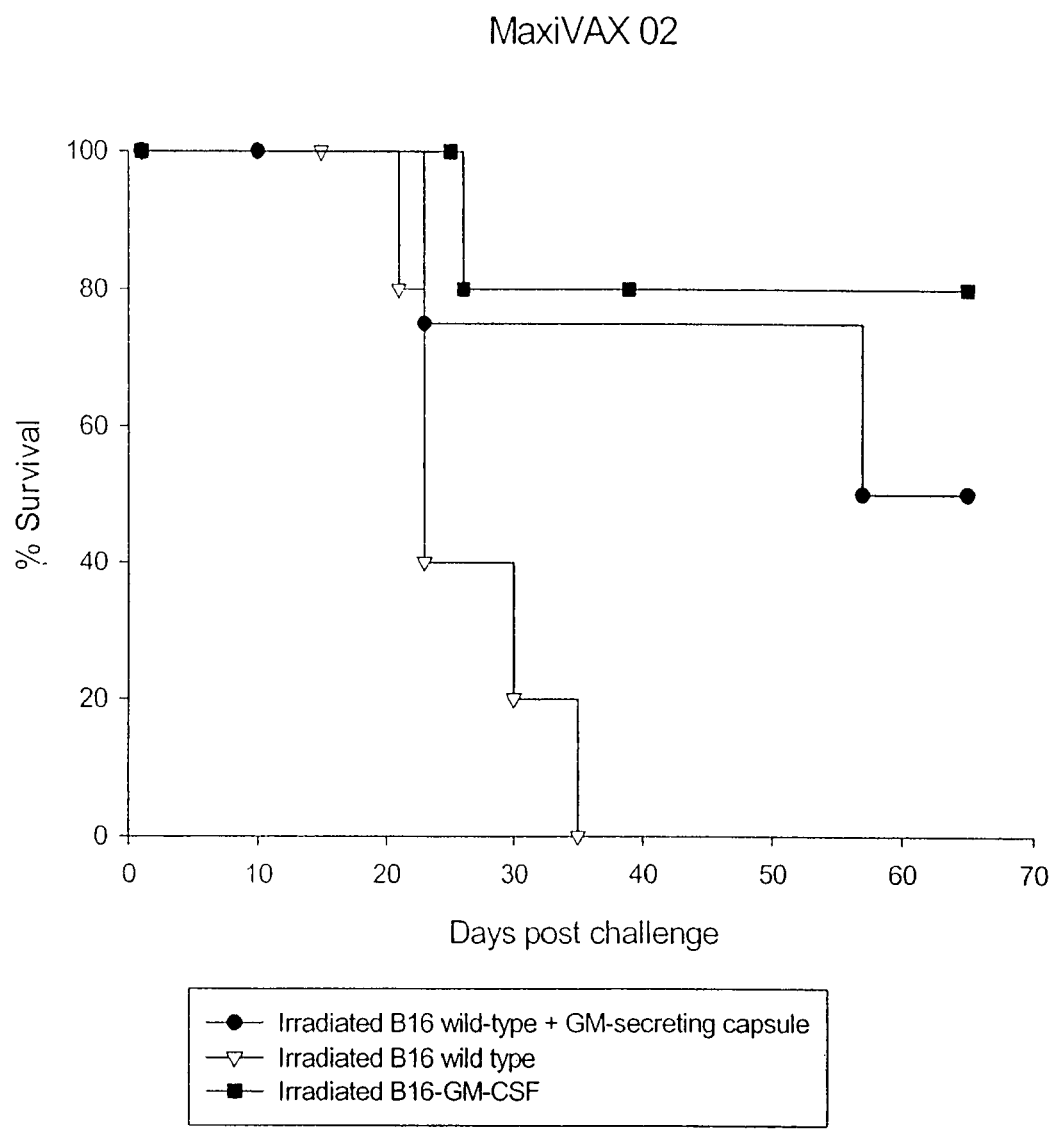

FIG. 5: Survival of mice after B16WT challenge.

The experimental conditions are identical to the conditions specified in FIG. 4 and exposed in example 4.

DETAILED DESCRIPTION

Definitions

In the context of the present application, the following terms are defined in the following manner:

An immunomodulator or an immunomodulatory agent is a compound or a composition which can enhance, amplify or decrease an immune response to an antigen or an immunogen.

An immunostimulatory agent or an immuno-activator is an immunomodulator which specifically enhances or amplifies the immune response to an antigen or an immunogen. In the context of the present invention, the term "immunostimulatory agent" or "immuno-activator" is used synonymously with the term "adjuvant".

Cells are considered to be immuno-isolated if, when introduced into a host, they are physically protected against the immune response of the host, i.e. there is no significant acquired or natural immune response against any cell components, including cell-surface antigens, secreted proteins etc., provided there is no physical contact between the cells and the effectors of the immune system. Consequently, no significant antibody or cell-mediated immune response to the cell is seen in the host organism.

Consequently, immuno-isolated cells are not attacked or destroyed by the immune response of the host, because they are undetectable by the immune system, which prevents any immune response against them and because they are physically protected against any immune response.

Encapsulation is a particular means of immuno-isolating cells in a device comprising a capsule of material, for example plastic, which is non-immunogenic for the host organism. Preferred polymers for the capsule are thermoplastic polyethersulfone (PES) hollow fibers (OD:720 µm; ID:524 µm, molecular weight cut-offs: 32 and 80 kDa; Akzo Nobel Faster AG, Wupperthal, Germany) and AN-69 polymer (acrylonitrile and sodium metallysulphonate anionic copolymer, Hospal R&D Int, Meyzieu, France). The capsules may have various shapes and sizes.

The present invention relates to encapsulated cells producing and secreting an immunomodulator (preferably GM-CSF), for use in therapy and in vaccination (preferably with cancer cells). Preferably, the encapsulated cells are engineered to produce the immunomodulator, although the invention also encompasses the use of cells and cell-lines which naturally produce the immunomodulator. It also relates to pharmaceutical compositions, vaccines and kits which can be used in this context. It finally relates to processes for vaccinating or treating patients.

In a first aspect, the present invention relates to cells which produce an immunomodulatory agent and which are physically immuno-isolated. The immunomodulatory agent produced is preferably a protein synthesized by the cells, but it can also be for example a cell-component such as a lipid, or an exogenous molecule further transformed by the cell, for example antigens processed by antigen-presenting cells or metabolites.

In a preferred embodiment, the immunomodulatory agent is immunostimulatory. Antigens are frequently too weak to trigger a significant immune response and some molecules involved in this response are known to enhance or amplify it.

An immunostimulatory agent may act in attracting Antigen-presenting cells, for example dendritic cells. It may also act in stimulating the activities of CD4 or CD8 T-cells.

Particularly potent immunostimulatory agents, which are preferred in the context of the present application, belong to the cytokine family. Preferred cytokines are IL-3, IL-4, IL-9, IL-1, IL-2, IL-7 (interleukine), transmembrane receptors of IFNγ, SCF (Stem Cell Factor) soluble or membranous, FL (Flt3 Ligand), G-CSF and GM-CSF (Granulocyte and Granulocyte-Macrophage Stimulating Factor), and combinations thereof. Particularly preferred immunostimulatory agents are FL and GM-CSF. Preferred cytokines are human cytokines, for example human GM-CSF.

In the context of cancer therapy, GM-CSF is particularly recommended as immunostimulatory agent because it has been identified as the most potent cytokine for activating systemic antitumor immunity (Dranoff et al, 1993).

In order to induce an adequate immune response, it can be very advantageous to combine several immunomodulatory agents in order to stimulate different pathways. A preferred combination is the association of GM-CSF and FL. Other combinations of 2 or more immunomodulatory agents are also envisaged by the present application.

Although the main role of an immuno-isolated cell of the invention is to produce an immunomodulatory agent, it can fulfil other additional functions. It can for example play a role in the detection of the magnitude or the localisation of the expected immune response. Another major additional function is to provide the antigenic agent. According to this variant, the same cell can produce both the antigenic agent triggering the response and the immunostimulatory agent enhancing the response. This is particularly advantageous in the case of antigen-based vaccination, or cell-based vaccination where the antigens are secreted or released from the cell membrane. This approach ensures that antigenic and immunostimulatory agents are co-localised.

In the case of cancer immunisation, the immuno-isolated cells of the invention are possibly chosen among cancerous cells expressing TAA (tumour associated-antigens) which preferably are lineage specific and tumour-specific.

Because the cells of the invention are immuno-isolated, the produced immunomodulatory agent is preferably soluble in order to be secreted and released. The same applies for the antigenic agents like TAA.

According to a particularly preferred variant, the source of immunomodulator, i.e. the immuno-isolated cells of the invention are dissociated from the source of antigenic agent. For example, according to this variant, a first cell or group of cells constitutes the antigen source and a second, immuno-isolated cell or group of cells constitutes the adjuvant source.

A preferred way to immuno-isolate cells is to provide a physical barrier "hiding" them from the general immune system. This goal can be achieved by a barrier device. Different barrier devices are suitable, in particular microcapsules and macrocapsules. The actions of encasing a cell or population of cells in such a barrier are referred to herein as microencapsulation and macroencapsulation, respectively.

Immuno-isolation overcomes the significant disadvantages associated with the implantation of free cells. In fact, the use of free cells generally requires immuno-suppressing drugs in order to protect them against the immune system of the host. By mechanically blocking immune attacks, barrier devices around grafted cells obviate the need for immuno-suppressive therapy. Moreover, the cells can be retrieved readily after a while, if need be. This last property allows a switchable release of the immunomodulatory agent. By retrieving the device, the release of the agent is stopped, which prevents unwanted presence of a molecule after the end of the immunization process. Capsules of the invention can be specifically engineered to facilitate their withdrawal, for example by incorporation of a string or other means to ease their retrieval.

Immuno-isolation also overcomes the significant disadvantages associated with the use of HLA-negative cells such as K-562 cell line which fails to express HLA class I or II antigens. Since the encapsulated cells are entirely protected against the immune system, they are not destroyed by innate or cellular immunity, whereas K-562 cells are involved in innate immunity rejection. The capacity of encapsulated cells to survive, to secrete protein for a prolonged period of time and to allow multiple immunizations is directly linked to the physical barrier of the capsule. Moreover, the amount of GM-CSF release into the patient after capsule implantation is not likely to differ from one individual to another depending on his or her innate immunity or immunosuppression. In contrast, the stability of GM-CSF release is likely to vary significantly not only in any given patient at the first and subsequent immunizations but also from one patient to another, with the injection of GM-CSF secreting K-562 cells.

The main property of the barrier device is to separate living cells from the immune system of the host by a synthetic, selectively permeable, non-immunogenic membrane.

The cells of the invention are living and preferably provide the chosen immunomodulatory agent on a long-term basis. For example, experimental results showed that encapsulated cells, engineered to secrete GM-CSF, do release GM-CSF outside the capsule for at least fifteen days. For this purpose, they must be supplied with all the factors necessary for their survival, their growth and the production of the immunomodulator of interest. In order to allow free exchange of nutriments, proteins, oxygen and biotherapeutic substances between exterior and interior, the device preferably is selectively permeable. Small molecules can transit via pores, especially molecules necessary for the survival of the cells, whereas high-molecular-weight substances such as immunocytes or antibodies are excluded. It moreover excludes inflammatory cells and thereby protects the encapsulated cells from tissue rejection.

Conversely, immunomodulatory agents produced by the cells of the invention can be delivered through the pores into the external medium. The diameter of the pores is preferably chosen in a range such that small molecules or proteins and immunomodulators are allowed to cross the barrier and that bigger ones like immunoglobulins are not, in order for the device to retain its immuno-protective property.

Clinical trials have already been performed showing that such immuno-isolation, using capsules, is very efficient, allowing the survival of allogeneic but also xenogeic (from other species) cells for many months without immune rejection. The efficacy of the physical immuno-isolation by a capsule has been validated by early clinical trial.

For the manufacture of microcapsules, a mixture of cells and sodium alginate are extruded, and solidified into beads generating a matrix which allows free exchange of proteins, nutriments and oxygen between encapsulated cells and the host. Advantages of this device include great surface to volume ratio and ease of implantation.

The macroencapsulation makes use of preformed macrocapsules, initially empty units that are loaded with a matrix and all the cells needed for treatment. The matrix is preferably a polymer, for example polyvinyl alcohol or a biopolymer like alginate. The matrix ensures a good ordering of the cells inside the capsule, specifically a homogenous distribution, and prevents agglutination at the walls. Macrocapsules are more durable and rugged than microcapsules, they contain internal reinforcements, can be tested for seal integrity before implantation and can be designed to be refillable in the body. They can also be retrieved simply.

Preferred polymers for the capsule are thermoplastic polyethersulfone (PES) hollow fibers (OD:720 µm; ID:524 µm, molecular weight cut-offs: 32 and 80 kDa; Akzo Nobel Faster AG, Wupperthal, Germany) and AN-69 polymer (acrylonitrile and sodium metallysulphonate anionic copolymer, Hospal R&D Int, Meyzieu, France).

The macrocapsules can have various sizes ranging from few micrometers to three to four centimeters. Depending on the size of the capsule and the size of the cells, as many as 200 000 cells can be loaded into a 1 cm device.

Particularly preferred devices of the invention are microcapsules and macrocapsules. According to the present application, cells of the invention produce a immunomodulatory agent. Either the cells naturally produce the agent, or this goal is achieved by modifying the cells. In a preferred case, cells are genetically modified to express the immunomodulatory agent. This is particularly convenient for many reasons.

By modifying a cell which normally may not produce the immunomodulatory agent, the use of cells of the invention is not limited to those naturally producing it. It is particularly advantageous that the agents are not limited to those naturally occurring. As it is known that mutated proteins sometimes exert improved activities, it is very advantageous to use this modified version of the protein instead of the wild-type one. It is also sometimes convenient to clone the soluble version of a membranous protein, in order to achieve its secretion.

Moreover, by genetically modifying cells of the invention, it is also possible to control the expression level of the immunomodulatory agent. A particularly attractive situation is the overexpression of the agent by cloning its sequence under the control of a promoter known to be very strong in the used cell. The modified cells become engineered factories producing high levels of immunomodulatory agent. The promoter can be chosen according to its activity such as to have a controlled level of immunomodulator expression. According to another embodiment, cells may be used which naturally contain the gene for the immunomodulatory agent, said gene being transcriptionally silent in that particular cell. Transcription can be activated by insertion of appropriate regulatory sequences, for example by homologus recombination. Inducible regulatory sequences which respond to specific stimuli such as substances, light, etc. . . . may also be used.

According to the invention, immunomodulatory agent-secreting cells secrete more than 10 ng/$10^6$ cells/24 hr of immunomodulatory agent. Preferred cells of the invention secrete a quantity of immunomodulatory agent equal or superior to 100 ng/10$^6$ cells/24 hr, preferably more than 500 ng/10$^6$ cells/24 hr. If needed, several capsules may be implanted simultaneously.

Consequently, a cell of the invention secretes more than 10×10$^{-15}$ g of immunomodulatory agent per 24 hr, preferably more than 100×10$^{-15}$ g/24 hr of immunomodulatory agent. A cell of the invention secretes for example between 80 and 960×10$^{-15}$ g/24 hr, preferably more than 500×10$^{-15}$ g/24 hr of immunomodulatory agent.

Concerning the best way to genetically modify the cells of the invention, methods and protocols are well known by one skilled in the art. Particularly preferred methods make use of engineered plasmids introduced by transfection and viruses introduced by infection. Retroviruses are well suited in the context of the present invention because they can be engineered to introduce a gene coding for the immunomodulatory agent into the genome of host cell.

As mentioned above, cells of the invention are not limited to cells naturally producing an immunomodulatory agent of interest. All sorts of cells can be used, particularly preferred are cells which are easy to transduce or transfect, and to culture and propagate. It is not necessary to use tumour cells as the by-stander immunomodulator producer. Based on the medical literature, different cell types can been used to produce for example cytokines. These include immortalized non-tumoral fibroblasts, myoblasts or tumour cells. Cells of the invention are advantageously endothelial cells or fibroblasts.

Particularly preferred cells are in general immortal cell lines. It is thus possible to genetically modify a cell line just once and to use cells from it for all applications of the present invention. Because the cells are immuno-isolated, they are not endangered by the immune system of the host, but they also do not endanger the other cells in their vicinity.

Another particularly interesting advantage is that cells are not necessary autologous with respect to the host. It is easier to employ allologeneic or heterologous cells, it can also be advantageous to use non-human animal cells, without prejudice thanks to the barrier device. Cells of the invention are preferably human cells.

The immuno-isolation of the cells is thus very advantageous over some prior systems because the sources of immunomodulatory agent can be considered as "universal" and not limited to a unique individual.

Cells of the invention are living. This ensures that the immunomodulator is continuously produced, for at least several days and even more if needed. In previous experiments using encapsulation, encapsulated cells engineered to secrete a protein have been implanted in patients for weeks or months. This long-lasting release overcomes the common problem of short half-life of immunomodulators.

According to a preferred immunization program, cells of the invention are implanted for a few days, preferably less than 12 days, for example between 4 and 10 days, for example between 5 to 7 days. Implantation of encapsulated cells for such a short period will not lead to marked fibrosis induced by the release of the immunomodulatory agent. Inflammation, at the vaccination site, around the capsule, will not induce a decrease of cell viability within the capsule and therefore it will not prevent the production and release of the immunomodulatory agent in that time frame.

Preferably, the cell-containing capsule is irradiated, for example by X-Rays, before implantation. Firstly, this irradiation ensures that, even if disruption of the capsule occurs, enclosed cells are not capable of propagation. Secondly, this irradiation ensures that the secretion of the immunomodulatory agent will stop after around 10 days, due to irradiation-induced cell death. This may be advantageous, should the secreted immunomodulatory agent generate a violent inflammatory response. Specifically, subcutaneous implantation of GM-CSF-secreting cells, encapsulated or not, could induce cutaneous necrosis if implanted during a period exceeding 15 days to 1 month. Irradiation of the capsule or cells before implantation does not prevent subsequent retrieval of the capsule.

In a preferred embodiment, cells of the invention are used in the context of cancer therapy. This product has been designated "Onco-Maxi Vax". Onco-Maxi-Vax is a therapeutic product (therapeutic vaccine) made of two components that are physically in close proximity during the immunization.

The first component of the Onco-Maxi-Vax system is the source of tumour antigens, this antigenic load is made of irradiated cells harvested from the patient to be treated, this component is specific for each patient. In order to ensure maximal antigen exposure the source of antigen is made of each patient's own tumour cells. These are harvested surgically or endoscopically from the patient, digested in order to obtain a cell-suspension and then irradiated at 10000 Rad before storage in aliquots in liquid nitrogen. Irradiation is a safety measure in order to prevent any growth of tumour cells that will be re-injected to the patients. This procedure has already been performed safely. This component of the Onco-Maxi-Vax system is unique to each patient, as it will be harvested from each individual and used in combination with the second component of the vaccine.

The second component of the Onco-Maxi-Vax vaccine is common (or "universal") to all patients, it is the immunomodulator provider. It is composed either of a large capsule (macro-encapsulation) or small capsules (micro-encapsulation) that contain living cells. The capsule(s) is (are) required to immuno-isolate allogeneic human cells. The capsule(s) is (are) semi-permeable. It allows the survival of the cells inside by nutrient migrations and it prevents cells exposure to an environment which would normally destroy them.

In the Onco-Maxi-Vax system, the cells to be encapsulated are genetically engineered to secrete immunostimulatory molecules. It should be seen as an immuno-isolated bio-reactor that produces and releases, at the site of vaccination, strong immuno-stimulatory signals. So far Granulocyte-Macrophage Colony-Stimulating Factor (GM-CSF) is probably the most potent immunostimulatory molecule for anti-tumor immune response. Because of bio-chemical properties GM-CSF needs to be produced locally at the vaccine site in order to obtain a sustained release of the protein for at least five to seven days. Initially the encapsulated cells are engineered to secrete GM-CSF only. Depending on synergistic studies, other immunomodulatory molecules can be added without difficulty (other cytokines such as IL-12, IL-15, IL-4, Interferon gamma, chemokines or dendritic growth factors).

To maximise safety, the capsule used in macro-encapsulation is retrievable and the cells that it contains are irradiated prior to implantation. Previous experiments have shown that irradiation of GM-CSF producer cells does not prevent the production and the release of the protein.

The two components of the Onco-Maxi-Vax vaccine are placed under the patient's skin in close proximity or in contact. They are implanted at sites distant from the primary tumour or metastasis in order to perform the vaccination in an immunologically un-disturbed location.

Five to seven days after the implantation, the capsule is removed, for example using an especially designed string attached to it. The autologous irradiated tumour cells injected as a component of the Onco-Maxi-Vax are progressively processed and removed by the patient's immune system, via naturally occurring mechanisms.

The vaccination treatment with Onco-Maxi-Vax comprises repeated immunizations at two to three week intervals at different sites, usually sub-cutaneous. The total number of vaccinations, although adjustable is preferably a minimum of five.

The dose of autologous cells is adjusted to the amount of cells harvested from the patients. It is recommended to have around $10^7$ to $10^8$ cells per immunization. When this dosage cannot be repeated 5 times, the dose of autologous tumour cells is reduced accordingly.

The ideal number of cells to be encapsulated is dependent on the amount of immunomodulatory agent such as GM-CSF that is required at the vaccination site. In previous studies, GM-CSF producing autologous cells were releasing between 80 to 960 ng/$10^6$ cells/24 hr. Release between 500 to 1000 ng/24 hr is considered a reasonable goal.

According to the invention, immunomodulatory agent such as GM-CSF-secreting cells secrete more than 10 ng/$10^6$ cells/24 hr of immunomodulatory agent. Preferred cells of the invention secrete a quantity of GM-CSF equal or superior to 100 ng/$10^6$ cells/24 hr, preferably more than 500 ng/$10^6$ cells/24 hr. If needed, several capsules may be implanted simultaneously. The total quantity of delivered immunomodulatory agent, especially GM-CSF, must be at least 1 microgram per 24 hours at the vaccination site.

Consequently, a cell of the invention secretes more than $10 \times 10^{-15}$ g of immunomodulatory agent per 24 hr, preferably more than $100 \times 10^{-15}$ g/24 hr of immunomodulatory agent. A cell of the invention secretes for example between 80 and $960 \times 10^{-15}$ g/24 hr, preferably more than $500 \times 10^{-15}$ g/24 hr of immunomodulatory agent.

Capsule according to the invention may contain between $2 \times 10^5$ cells and 2, 3, 4 or $5 \times 10^7$ cells, preferably more than $10^7$ cells per capsule, for example $2 \times 10^7$ cells per capsule.

This anti-tumour immunization is performed for a wide range of tumour types. As discussed above, the encapsulated cells are identical for every patient. Only in patients with tumour cells that can be harvested from a solid primary tumour, a metastasis or from fluid containing tumour cells (pleural, peritoneal, bone marrow or blood) is it possible to generate the full vaccine product.

In clinical oncology, most of the patients present a primary tumour or metastatic lesion. Not all tumours or metastases are equally easy to process. Therefore the type of tumour that will be tested needs to fulfil various criteria in terms of feasibility. Cancers that are likely to have a primary tumour that can be harvested are:
 Central Nervous System tumour such as Glioblastoma
 Lung tumour (non-small cell lung cancer)
 Prostate tumour
 Gastric carcinoma
 Breast carcinoma
 Lymphoma
 Pancreatic carcinoma
 Hepatocarcinoma (Liver tumour)
 Colon carcinoma
 Renal cell carcinoma
 Ovarian carcinoma
 Uterine carcinoma
 Sarcoma (soft tissue)
 Leukemia (lymphnode or blood)
 Multiple myeloma (blood, bone marrow, lymph-node, soft tissue)

Cancers that are likely to have metastases that can be harvested are dependant on the location of the metastasis. For technical reasons it is more difficult to harvest bone metastases than other localizations. These cancers may be for example:
 Head and neck carcinoma (lymph-node metasatasis)
 Lung cancer (lung, liver, soft tissue, brain, adrenal metastasis)
 Prostate (non-bone metastasis)
 Breast carcinoma (lung, liver, soft tissue, pleural fluid)
 Gastric carcinoma (liver)
 Pancreatic carcinoma (liver)
 Colon carcinoma (liver)
 Melanoma (lung, lymph-node, soft tissue, liver, brain)
 Renal Cell carcinoma (lung, liver)
 Ovarian carcinoma (peritoneal or pleural fluid, liver)
 Germinal tumors (lung)
 Bladder carcinoma (liver, lymph-node)

In addition to these requirements, patients to be enrolled in a phase I study must have failed or refused standard treatment for their cancer type and their tumour stage.

Regarding this aspect, the following tumours could be preferably treated with Phase I Onco-Maxi-Vax after the specified treatment:
CNS tumour (glioblastoma): Relapse after surgery+/−radio-chemotherapy;
Head and neck tumor: Metastatic disease after surgery+/−radiotherapy;
Lung cancer: NSCLC/Mesothelioma: First line metastatic disease or after progression post chemotherapy;
Small cell lung cancer: In metastatic patients after first line of chemotherapy for either localized or extensive disease;
Breast/Ovarian cancer: After two lines of chemotherapy for metastatic disease;
Esophagus/Gastric/Colon carcinoma/Bladder, Uterine cancer: Metastatic, progressing after one line of chemotherapy;
Pancreatic/Hepato-cellular cancer: Post-surgery when incomplete or with loco-regional or distant metastasis;
Renal cell carcinoma/Melanoma: Metastatic disease first line;
Lymphoma/Multiple myeloma/Leukemia: Progression despite multiple chemotherapy regimen in advance disease, not treatable with currently available recognized therapy (autologous bone marrow re-infusion, antibody);
Sarcoma, germinal tumors: Progresive disease after multiple chemotherapy regimens;
Prostate cancer: after failure of hormone therapy and when metastasis can be harvested (liver, lymph-node, others.)

In order to evaluate potential response using classical radiological criteria, patients must have measurable disease or evaluable disease. Follow-up period is until progression of disease. Follow-up includes radiological studies mainly with CT scan to record any change in tumour volume.

Toxicity and feasibility are recorded during the immunization period and also during the follow-up period by bi-weekly visit at the Oncology center and evaluation by an oncologist.

Serological tumour markers such as CA 153, CA19-9, CEA, AFP, NSE, CA 125, are monitored when elevated prior to vaccination.

Whenever possible surgical resection of metastasis are attempted in order to document any changes in tumour structure. It is well described that classical tumour evaluation by bi-dimensional measurement may not be the best evaluation method to assess potential efficacy of immunization treatment. Destruction of the tumour cells can be very efficient and replaced with fibrous or inflammatory cells without detectable changes in size on radiological examination. Metabolic activity as assess by PET scan may be of relevance in this setting. The analysis of post immunization tumour lesion is of great interest for immunological analysis such as the characterization of the potential tumour antigen targeted by the treatment.

In another preferred embodiment, cells of the invention are used in the context of immunisation against various infectious diseases. This product of the invention can thus be named "IA-Maxi Vax" (infectious agent).

Similarly to the Onco-Maxi-vax approach "IA-Maxi-Vax" is a therapeutic product (vaccine) made of two components that are physically in close proximity during the immunization.

One component represents the source of antigen(s). For this anti-infectious vaccination the antigen comprises one or more components from the infectious agents. Therefore all patients with a specific infection will be treated with the same product. Many known antigen components have been described in infectious diseases caused by viral, bacterial or parasitic pathogens and are used currently for immunization strategies. These antigens can be used as inactivated pathogens, infectious agent's lysates, protein extracts, recombinant proteins, peptides, DNA or other forms. In some conditions depending on the infectious agent or the host medical condition immunization is weak or non-protective leading to significant morbidity or mortality.

HIV is an example of failure to naturally eradicate a viral pathogen.

Immunosuppression after bone marrow transplantation is an example where the usually benign CMV infection can be life-threatening.

The first component of the vaccine comprises a combination of the antigen or a pool of antigens. Encapsulated, bystander cells of the invention that release locally, at the vaccination site, a very potent immunomodulatory signal constitute the second component of the vaccine.

The second component of the vaccine is the same ("universal") for all patients. It is made of a semi-permeable capsule (macro or micro) that contains live cells. The capsule is required to immuno-isolate allogeneic human cells. It allows the survival of the cells inside by nutrients migrations and it prevents cells exposure to the environment that would normally destroy them.

The cells to be encapsulated are genetically engineered to secrete immunostimulatory molecules. So far Granulocyte-Macrophage Colony-Stimulating Factor (GM-CSF) is probably one of the most potent immunostimulatory molecule for boosting the immune response. GM-CSF has been shown to increase immunity against various parasitic or viral agents. Because of bio-chemical properties GM-CSF needs to be produced locally at the vaccine site in order to obtain a sustained release of the protein for at least five to seven days. Initially the encapsulated cells are engineered to secrete GM-CSF only. Depending on synergistic studies, other immunomodulatory molecules could easily be added (other cytokine such as IL-12, IL-15, IL-4, Interferon gamma, chemokines or dendritic cells growth factors)

To maximize safety, the capsule is retrievable and the cells that it contains are irradiated prior to implantation. Previous experiment have shown that irradiation of GM-CSF producer cells does not prevent the production and the release of the protein.

The two components of the infectious-agent vaccine need to be placed under the patients skin in close proximity or contact. It may be beneficial to have sequential administration of the two components, the capsule being implanted first, followed by the antigenic stimulus.

Five to seven days after the implantation the capsule is removed, for example using an especially designed string attached to it.

The vaccination treatment with "IA-Maxi-Vax" comprises repeated immunizations at two to three week intervals at different sites, always sub-cutaneous. The total number of vaccination is dependant of the protocol and dosages and must be adjusted in each particular case.

The "IA-Maxi-Vax" addresses non-exhaustively the following conditions:
Viral Infections:
Target: HIV patients at various stage of their disease (early stage may be better candidates, with stronger immune system)
Target: CMV infection in specific condition (pre or post organ transplantation)
Target: recurrent herpes infection
Hepatitis B or Epstein Bar virus
Hepatitis C
Bacterial Infections Such as:
Target: Mycobacterial infection is specific population such as HIV patients
Target *Elicobacter pylori*. *E. Pylori* is the causative agent in the majority of the stomach ulcer or gastritis.
Parasitic Infections Such as
Malaria, Toxoplasma, Pneumocystis.

According to a second aspect, the present invention relates to pharmaceutical compositions, vaccines and kits comprising cells which produce an immunomodulatory agent and which are physically immuno-isolated.

All these products are particularly well suited for industrial production because they are easy to produce in large amount thanks to the 'universal' characteristic of the device. As the cells are immuno-isolated, the same encapsulated cells are suitable for all the patients. This 'universal' characteristic is particularly interesting for cancer therapy where multiple injections of the vaccine or the pharmaceutical composition are required.

A pharmaceutical composition according to the present invention comprises immuno-isolated cells producing an immunomodulator combined with a physiologically acceptable carrier. The density of cells of the invention to incorporate in the composition must be defined for each different case. In particular, the density of cells to incorporate is function of the immunomodulator dose required. Examples of suitable physiologically acceptable carriers would consist of a device that would fulfil the following needs: non-toxic (local and systemic), efficient immuno-isolation, permeable allowing sustained release of the immuno-modulator. A macro or microcapsule made of PES or AH-69 fulfil these requirements as well as the products developed by Theracytes Inc.

A vaccine composition of the present invention comprises immuno-isolated cells producing an immunomodulator combined with an antigenic component. This second component of the vaccine represents the molecule against which an immunization reaction is expected. The first one secretes the immunomodulator necessary for enhancing the immunization process. The antigenic component can be represented by a protein, for example a viral protein which is known to be immunogeneic, or by a whole cell expressing antigens at its surface, or by an extract containing several antigenic substances. In the context of cancer, the antigenic component is preferably a tumour cell (therapeutic vaccine).

Tumour cells are known to express at their surface tumor-associated antigens against which an immune response is desired.

When tumour cells are used, as in the cancer context, the tumour cells are preferably irradiated before incorporation into a composition. Irradiation is a safety measure in order to prevent any growth of tumour cells that will be re-injected to the patients. In addition to safety, irradiation may be a very good way to allow the release of potentially useful antigenic determinants.

In the context of vaccination against infectious agents, the antigenic component is preferably from the agent against which an immune response is desired, for example from a virus. Preferred viruses are Hepetitis C and HIV.

The present invention also provides kits comprising immuno-isolated cells producing an immunomodulator combined with an antigenic component. The first component of the kit secretes the immunomodulator necessary for enhancing the immunization process against the second antigenic component.

As already mentioned for the vaccine composition, the antigenic component of a kit according to the present invention preferably comprises a cell producing, secreting or releasing an antigen. Alternatively, the antigenic component can be a molecule, for example a protein, or a cellular extract.

In the context of cancer, the antigenic component of the kit is preferably a tumour cell. The same safety measures are preferably taken by irradiating the tumour cell before use.

According to the present invention, the kit will generally be used for implantation into human body. For this reason, many constraints are imposed on the properties of the kit. In particular, this kit must be designed to be as small as possible. It must also be biocompatible. A kit according to the invention can be placed for a time as long as several weeks or months. The kit must be safe throughout the duration of this period. In particular, in numerous uses of the kit, the encapsulation device needs to be sealed.

According to a third aspect of the present application, the invention encompasses uses of immuno-isolated cells producing an immunomodulatory agent, and uses of pharmaceutical compositions, vaccines and kits as described above in the therapeutic domain as well as in the vaccination field.

The invention relates in particular to a process for vaccinating a subject in need of such a treatment. This process comprises the administration of a composition comprising cells of the invention. The subject is preferably a human patient, but animals are also possible. A subject can be in need of vaccination for different reasons, because a preventive immunization is preferable, like for benign disease, or is necessary for example in the case of severe epidemics.

In a preferred case of vaccination, the immune response is raised against a particular antigenic component. In this predominant case, the process of the invention comprises also the step of administrating the antigenic component to the subject.

A patient can be preventively vaccinated because he will be in contact with the antigenic component sooner or later. He can also be therapeutically immunized by the process of the invention because he is already in contact with the antigenic component but not able to generate an adequate immune response by himself.

When the process comprises the administration of cells of the invention and of an antigenic component, different protocols are envisaged. Both administrations can be made simultaneously, or they can be made separately, or sequentially. It can be very advantageous to temporally dissociate the administrations. In fact, cells of the invention, thanks to their barrier device, have a long-lasting effect. On the contrary, antigenic components injected are likely to be processed and eliminated very rapidly by the host immune system. In such a case, when administrations are dissociated, the administration of antigenic component can be repeated whereas there is a single administration of cells of the invention.

The antigenic and the immunomodulatory agents should preferably be co-localised in order to produced an optimised effect.

Preferably, cells of the invention are irradiated before administration. When the immuno-isolation consists in a capsule, it is preferred to irradiate the capsule. This irradiation step is preferably done shortly prior administration, but may occur a few days before.

Preferably, for an optimised immunization process, the administration is repeated several times, preferably the administrations of cells of the invention as well as antigenic component are repeated. In a preferred case, the administration is repeated more than twice, preferably between 3 and 6 times, preferably 5 times.

It is crucial that the repeated immunisations must not generate an increased immune response against the immunomodulator or its means of delivery, at the risk of annulling the benefit of the repeated immunisations or generating a dangerous immune response. The immuno-isolation device of the cells producing the immunomodulator, as proposed in the present application, avoids these problems. It represents a technical advantage over the systems developed in the prior art.

As discussed above, when the vaccinating process of the invention is used in the field of cancer, the antigenic component is preferably a whole tumour cell, advantageously irradiated. Because it is known that some antigens are present on many tumours from the same lineage, the used tumour cells may be an allogeneic ones. However, the tumour cells are preferably autologous with respect to the patient.

Preferably, the tumour cells, which are the source of antigenic component, and the immuno-isolated cells, which are the source of immunomodulatory component, are distinct. This situation is advantageous over the prior systems coupling both, because the tumour cells need not be manipulated, except the harvest and irradiation steps, contrary to prior solutions requiring genetic manipulation of the tumour cells.

The administration mode of cells of the invention, according to the present process, is chosen to be the most efficient. In particular, the mode is adapted to the desired localisation for the cells and the antigenic component. A preferred localisation is sub-cutaneous because this region is rich in dendritic cells. The administration can be made intradermally. Other localisations likely to favour the expected immune response are also preferred.

According to the invention, the immunomodulatory secreting cells are loaded in a capsule, which is to be implanted. In a preferred embodiment, the capsule is removed after 2 to 7 days, preferably after 5 to 7 days.

The invention also relates to a process for treating a patient suffering from cancer. Particularly well suited cancers and states are described in detail above. This process comprises the administration of a composition containing immuno-isolated cells producing an immunomodulatory agent. According to the present invention, the immuno-isolated cells may be autologous or allogeneic, in particular, they may be autologous tumour cells.

The administered composition may be injected, ingested, implanted, applied, or any other administration means. The composition may comprises any pharmaceutical additive necessary for the survival of the cells and for the success of the administration or implantation. The composition may also contain an antigenic component which is generally irradiated whole tumour cells. It is preferably administrated at a site distant from the tumour location, where no previous immune response is supposed to have taken place. However, the composition may be administrated in the vicinity of tumour cells of the patient to be treated.

In the context of the present invention, immuno-isolated cells, producing or secreting an immunomodulatory agent, as described above, are used in therapy, particularly in cancer therapy. These cells are also possibly used in the field of vaccination.

Another use which is perfectly adapted to the cells of the invention, is in the manufacture of an adjuvant. In this particular case, the function of the adjuvant is to enhance an immune response which is considered too weak. If so, the immunomodulatory agent produced by the immuno-isolated cells of the invention is an immunostimulator.

Another use is in the manufacture of a medicament for the prevention or the treatment of cancer. The characteristics of such an application are already well documented above.

Kits comprising cells of the invention are described above. The present application also envisages the use of at least one of these kits for the manufacture of a vaccine.

EXAMPLES

Example 1: Testing the Secretion of Human GM-CSF Release by Various Cells Lines after Transfection This example shows the ability of different cell lines to secrete human GM-CSF with and without being irradiated.
Transfection Methods:
Human GM-CSF cDNA was cloned into a retroviral vector (MFG) as described in the literature (Danos Olivier and Mulligan Richard 1988 PNAS Vol. 85 p 6460-64; Jaffe Elizabeth et al. 1993 Cancer research Vol. 53 p 2221-26).

The human GM-CSF is inserted in-frame into the retroviral vector. The MFG-hGM-CSF construct was sequenced in order to ensure correct in-frame cloning.

Using transient transfection technique with lipofectamine MFG-hGM-CSF construct was transfected into 293-gpg cells as described in the literature (Ory Daniel et al. 1996 PNAS Vol. 93 p 11400-06). With adequate selection, these cells produce pseudotyped retroviral particle containing the hGM-CSF gene. These viral particles are replication defective but can infect a wide range of mammalian cells.

The supernatant of transfected 293-gpg cells is used to infect dividing cells. This is performed with polybrene and no selection is performed. Therefore the whole cell population is used for subsequent analysis.
Tests for Secretion:
The infected cells are then tested for their ability to secrete human GM-CSF.

A classical ELISA is performed to measure the amount of GM-CSF in the supernatant of the various cell type tested.

Murine and human cell lines were tested for their ability to secrete human GM-CSF at various time points and also after irradiation 3500 rads. The different tested cell lines are the following:
Renca: murine renal cancer cell line from Balb/c background B16 F10: melanoma cell line from C57BL/6 background
Cell line A: human tumorogenic fibroblasts
Cell line B: human immortalized fibroblasts $10^6$ cells are plated on a culture dish. After 48 hours the supernatant is harvested and 0.2 u filtered and frozen at −20° C. For Elisa the antibodies and the protein standards are purchased at R&D system.

Non-transfected cells are also tested as negative control.
Results:
The Results are expressed in ng of h-GM-CSF by $10^6$ cells at 48 hours

|  | no irradiation | irradiation |
|---|---|---|
| Renca wt | 0 | 0 |
| B16-wt | 0 | 0 |
| Renca h-GM-CSF | 23400 | 9300 |
| B16-h-GM-CSF | 37650 |  |
| Cell line A | 0.9 |  |
| Cell line A h-GM-CSF | 18600 | 14900 |
| Cell line B | 1.2 |  |
| Cell line B h-GM-CSF | 6300 | 2950 |
| Media only | 0 | 0 |

Murine cancer cell lines and human fibroblast cell lines are able to secrete large amount of human GM-CSF for prolonged period of time in-vitro. No decrease has been observed in the production with time (at least three weeks after infection, for non-irradiated cells).

Altogether these experimental data show that human fibroblasts can secrete high level of human GM-CSF for several days without obvious toxicities to the cells. They are therefore good candidates for the clinical application as suggested in the Maxi-Vax approach; that is encapsulated, immunoprotected, allogeneic cells releasing immunomodulator at the vaccination site.

Example 2: Experimental Protocol Assessing the Efficacy of Onco-Maxi-Vax. Autologous Irradiated Tumour Cells+Encapsulated GM-Producers Cells. Pre-Clinical Development in Mouse Model This example concerns the reproduction, using Onco-Maxi Vax, of the vaccination efficacy observed in the classical setting, when GM-CSF is produced by the irradiated tumour cells, in both wild-type mice and GM-CSF deficient mice. It also enables documentation of any new toxicity related to the use of the capsule, its manipulation or the cells it contains.

Furthermore, characterization of the response by standard techniques (Histology of vaccine site, cytokines profile, dendritic cell staining at the vaccination site) is carried out.
Experimental Design
A) Measurement of in-vitro release of murine GM-CSF from the capsule containing GM-CSF secreting cells.
This is performed with standard monoclonal antibodies against murine GM-CSF in Enzyme-Linked immunoabsorbent Assays (ELISA). (R&D systems). The amounts of protein released as well as the reproducibility from one capsule to the others are assessed and results are shown in FIG. 3.
B) Direct comparison of the two immunization procedures:
The negative control group: Vaccination with irradiated, unmanipulated wild-type B16 melanoma cells (B16 WT).
The positive control group: The standard technique used in the laboratory: Vaccination with irradiated, GM-CSF secreting B16 melanoma cells. (B16-GM)

The investigational group: Vaccination with irradiated, un-manipulated B16 melanoma cells (B16 WT) in close contact with a sub-cutaneoulsy implanted capsule containing cells releasing murine GM-CSF.

The vaccine combines irradiated wild type B16 melanoma cells injected in close contact to macrocapsule made of PES (polyethersulfone). This capsule contains 200 000 Renca cells retrovirally engineered to secrete GM-CSF. The encapsulated cells are mixed with a collagen-based matrix.

The B16 GM and the Renca GM cells are generated using the same transfection technique. Briefly, the murine GM-CSF cDNA was inserted into the MFG retroviral vector. Retroviral particles containing the mGM-CSF cDNA were obtained after lipofectamine transfection of 293-CPG cells. This infectious, non-replicative retroviral particles were harvested, centrifuged, concentrated and used to infect B16 and the Renca cells respectively. The amount of GM-CSF released by the B16-GM and the Renca-GM is measured by standard Elisa technique.

Three additional groups to study the potential effect of the capsule itself.
   a) The positive control group+capsule containing non-secreting cells, to test if the capsule decrease the effect.
   b) The negative control group+capsule containing non-secreting cells, to test if the capsule have an effect by itself, without GM-CSF.
   c) Vaccination with encapsulated GM secreting cells only, to test if the GM-CSF+allogeneic cells have any effect.

These three additional groups ensure that the effect observed with the investigational arm is GM-CSF dependant and tumour specific.

Protocol

Mice: C57Bl/6 strain at least 8 weeks of age

Cells: Culture in DMEM media with 10% inactivated calf serum+penicillin and streptomycin. Harvest from cell culture plates is performed one to two hours before injection. B16 WT and B16 GM adherent cells are washed with PBS ×1, detached with Trypsin EDTA (Life tech) then washed ×3 in HBSS. Cells are then counted and resuspended in HBSS at the described concentration.

Renca GM and Renca Wt are the cells loaded into the capsules. These cells are cultured in the same DMEM media as above.

Day 0: Vaccination:

B16-WT or B16 GM are harvested, resuspended at the concentration of $2\times10^6$/ml and irradiated at 3500 rad. Capsules are implanted subcutaneously on the abdomen in the appropriate groups after irradiation (3500 rad).

Vaccination is performed sub-cutaneously with $1\times10^6$ cells into 500 ul on the abdomen. Groups with the capsule and the B16 cells co-injection, the cells are injected in close contact with the capsule. Superficial anesthesia is used to ensure reproducibility of the procedure.

Day 7: Challenge:

B16 WT are harvested from culture dishes and resuspended at a concentration of $1\times10^6$/ml. Injection of $5\times10^5$ cells in 500 ul is performed on the upper-back.

Superficial anesthesia is used to ensure reproducibility of the procedure.

Follow-up.

Animals are checked daily for tumour growth. Day of visible tumour is recorded Animal are sacrificed when tumour is larger then 1 cm or ulcerates. Day of sacrifice is recorded. Tumour free animals are observed until day 80 for potential late tumour growth.

This model has been well described in the past and the mice that do not develop tumour at the sub-cutaneous challenge site will not develop distant metastasis.

Mice free of tumour at day 80 have long-lasting specific anti-tumour immunity as long as the control groups gave the results that allow validation of the experiments.

Preliminary Results:

Toxicity evaluation of the prolonged GM-CSF release by the encapsulated cells and of the capsule by itself under the skin. This is assessed by the analysis of mice with implanted capsule containing increasing numbers of irradiated GM secreting cells. The effect of empty capsule is also analysed. This is performed by observation of the animal for any local or systemic toxicity. Serum level of GM-CSF are assessed by ELISA. Histological analysis is performed on the vaccination site. This toxicity evaluation is performed with 2 mice per group.

Example 3: Protocol for the Preparation of "Onco-Maxi-Vax" for Use in Humans

This example concerns the preparation of Onco-Maxi Vax, for the vaccination of a human patient. The protocol gives detailed information regarding the preparation of the antigenic load, the generation of the immuno-isolated cytokine provider and the immunization with the two components from the Onco-Maxi-Vax.

Every step of the vaccine preparation for the two components (irradiated autologous cells and encapsulated GM-CSF producing cells) and the immunizations are performed according to clinical GMP guidelines.

1) Harvest of Autologous Tumor Cells (Antigenic Load)

A tumour mass (primary lesion or metastasis) from the patient to be treated is surgically harvested. An standard pathological examination is performed on a portion of the mass in order to confirm the malignant nature of the harvested material. It is then processed in order to obtain a single cell suspension. This is performed by both mechanical and enzymatic methods.

The tumour mass is first cut in smaller pieces using dissecting microscope, then the tumor is put into a sterile bag with a sterile solution containing various enzymes (collagenase). The bag is inserted into a cell blender (Stomacher Lab System) that will process the product into a cell suspension. The combination of enzymatic and mechanical activities at 37° C. for few hours allows the efficient dissociation of the extra-cellular matrix of the tumour and turn it into single cell suspension. This is performed in serum free solution.

The cells are then washed three time with HBSS using a refrigerated centrifuge (Sorvall) 4° C., 5 minutes, 700 rpm, and resuspended in HBSS. Cells are then counted using Trypan blue (Fluka) solution and a Neubauer chamber.

The cells are resuspended at a chosen concentration, irradiated at 10000 rads in an irradiator devoted for clinical use, aliquoted and frozen in freezing media containing 10% DMSO.

2) Immuno-Isolated Cytokine Provider
   a) Generation of GM-CSF Producing Cells.

The cells to be introduced into the capsules are allogeneic (obtained from a human cell line). In order to prevent un-predicted toxicity, we use cell lines that have already been approved in clinical protocols such as immortalized fibroblasts or myoblasts. These cells are first stably transfected with human GM-CSF cDNA.

Two methods of transfection can be used: retroviral and electroporation. For retroviral transfection, hGM-CSF cDNA is inserted in-frame into the MFG retroviral vector and transcription is driven by the LTR of the virus. The plasmid does not contain any selection marker or antibiotic resistance gene.

For the transfection by electroporation, hGM-CSF cDNA is under the CMV promoter and the plasmid contains a selective marker (such as an antibiotic resistance gene).

The invention therefore includes the use of different types of cells for transfection and of different GM-CSF plasmids. This leaves more flexibility with respects to local health department regulations.

The cytokine producing cells is cultured in serum free media at 37° C. with 5% CO2 using standard techniques. Harvesting is performed as follow: The supernatant of confluent, adherent cells in a 10 cm culture plate is removed and the cells are washed once with 5 ml of autoclaved Phosphate buffered Saline (PBS) for 5 minutes at 37° C. PBS is then removed and 2 ml of Trypsin-EDTA 0.5% (Life Technologies N° 25300054) is added and the cells are incubated for four minutes at 37° C. The trypsin/EDTA allows the detachment of the adherent tumor cells. The cells are then harvested with a 2 ml pipet and diluted into 5 ml of Hank's balanced salt solution (HBSS Life Technologies N° 24020091). The cells are washed three time with HBSS using a refrigerated centrifuge (Sorvall) 4° C., 5 minutes, 700 rpm) and resuspended in HBSS. Cells are then counted using Trypan blue (Fluka) solution and a neubauer chamber.

The quantity of hGM-CSF produced and secreted by the cells is evaluated Elisa (R&D system and Pharmingen kits) on filtered cell's supernatant. This analysis allows the selection of the best cytokine producing cell-line.

b) Immuno-Isolation of Cytokine Producing Cells

In order to ensure sustained release of cytokine by allogeneic cells and allow repeated immunization it is necessary to immuno-isolate the cytokine producing cells from the recipient's immune system. This is performed by either macro or micro-encapsulation.

The cytokine producing cells are loaded into macrocapsules or embedded in microcapsules. The capsules can be made of various polymers with various sizes and pores, such as PES and TF10/10 capsules with and without PVA (polyvinyl alcohol) matrix. The capsule is loaded with the cell suspension at a rate of 10.5 ul/min Sealing of the capsule is obtained by polymer glue, but can also be done by heating or surgical clips. Analysis from supernatant of encapsulated cells containing GM-CSF secreting cells showed that a stable, continuous release of GM-CSF is achieved for at least fifteen days after loading, with cytokine levels that are around 70 ng/$10^5$ cells/24 hrs.

3) Immunization:

Immunization with Onco-Maxi-Vax requires the subcutaneous injection in close contact of the two components of the vaccine.

The capsule containing the cytokine producing cells is placed in the sub-cutaneous tissue using a small skin incision under local anaesthesia. The skin is closed with surgical tape.

The irradiated tumor cells from the patient (=antigenic load) are thawed, washed two time with 0.9% NaCl, sterile solution and then injected, sub-cutaneously, in very close vicinity to the capsule, using a 24 gauge needle.

Vaccination is repeated every two weeks four times (and more if enough autologous tumour cells are available). The site of vaccination is different at each immunization (abdominal wall, upper arms, thighs, thorax, etc).

Example 4: Onco-Maxi-Vax. Autologous Irradiated Tumour Cells+Encapsulated GM-Producers Cells. In Vivo Results in Mouse Model Showing Survival at 50 Days after B16WT Challenge This example concerns in vivo data in mice, which are protected from death induced by the melanoma tumor cell line B16.

Protocol

Mice: C57Bl/6 strain at least 8 weeks of age

Cells: Culture in DMEM media with 10% inactivated calf serum+penicillin and streptomycin. Harvest from cell culture plates is performed one to two hours before injection. B16 WT and B16 GM adherent cells are washed with PBS ×1, detached with Trypsin EDTA (Life tech) then washed ×3 in HBSS. Cells are then counted and resuspended in HBSS at $2\times10^6$ cells/ml for vaccination and $4\times10^5$ cells/ml for tumor challenge.

Renca GM (GM-CSF secreting Renca cells) are the cells loaded into the capsules. The capsules were PES capsules with PVA (polyvinyl alcohol) matrix. These cells are cultured in the same DMEM media as above.

Three groups of 5 mice C57BL/6 are immunized.

Group 1 (Negative control group): Mice are treated with irradiated, encapsulated GM-CSF secreting Renca cells only (no B16 melanoma cells).

Group 2 (Study group). Mice are immunized with the same irradiated encapsulated Renca-GM-CSF cells plus irradiated B16 wt melanoma cells.

Group 3 (Positive control group). Mice are immunized with irradiated, non encapsulated B16 melanoma cells engineered to secrete GM-CSF.

Mice were immunized with either irradiated capsule only (group 1), capsule+irradiated B16 wt (group 2) or irradiated B16-GM-CSF (group 3) on day −7. Each capsule containing $10^5$ GM-CSF secreting Renca cells was irradiated (3500 rad) prior to implantation. Mice from groups 1 and 2 were implanted with 2 capsules each, put sub-cutaneously in a V-shape on the abdomen. After 3 hours, the groups 2 and 3 were injected with irradiated B16 cells, $10^6$ B16 wt cells for group 2, $10^6$ B16-GM-CSF cells for group 3, sub-cutaneously between the two capsules.

On day 0, all the mice were challenged with live B16 wt $2\times10^5$ cells on the upper back.

Mice with growing tumor superior to 1 cm or showing tumor ulceration were sacrificed. All these were tumor-related. Non-sacrificed mice remained tumor-free. Survival represents percentage of tumor-free mice in each group.

This animal experiment shows a very good efficacy of encapsulated GM-CSF secreting cells on survival at 50 days (see FIG. 4).

This experiment was repeated and the results are shown in FIG. 5 with a different graphical representation. This second experiment also illustrates the efficiency of vaccination with encapsulated GM-CSF secreting cells on survival over more than two months.

The invention claimed is:

1. A vaccine composition comprising two components:
a) a first component comprising at least one macrocapsule comprising between $2\times10^5$ and $5\times10^7$ immuno-isolated allogeneic human cells that secrete at least 10 ng/24 hours of an immunostimulatory agent for at least 5 to 7 days, wherein the immunostimulatory agent is GM-CSF and wherein the macrocapsule is retrievable; and b) a second antigenic component comprising a population of tumour cells from the patient to be treated, wherein said tumour cells are irradiated to prevent growth of said tumor cells.

2. The vaccine of claim 1, wherein said immuno-isolated cells further produce another immunostimulatory agent.

3. The vaccine of claim 2, wherein said second immunostimulatory agent is selected from the group consisting of IL-12, IL-15, IL-4, Interferon gamma, chemokines, and dendritic growth factors.

4. The vaccine of claim 1, wherein said macrocapsule is selectively permeable.

5. The vaccine of claim 4, wherein said macrocapsule is selectively permeable to molecules with molecular weight smaller than 280 kDa.

6. The vaccine of claim 1, wherein said immuno-isolated cells are genetically modified to express the immunostimulatory agent.

7. The vaccine of claim 6, wherein the genetic modification is achieved by transfection by a plasmid or infection by a virus.

8. The vaccine of claim 1, wherein said immuno-isolated cells are a human established cell line selected from the group consisting of a fibroblast and an epithelial cell line.

9. The vaccine of claim 1, wherein said immuno-isolated cells are immortal or immortalised.

10. The vaccine of claim 1, wherein said immuno-isolated cells are non-tumoral.

11. The vaccine of claim 1, wherein the immuno-isolated allogeneic human cells that secrete between 500 and 1000 ng/24 hours of the immunostimulatory agent.

12. A pharmaceutical composition comprising the vaccine of claim 1 and a physiologically acceptable carrier.

13. A kit comprising the vaccine of claim 1.

14. A method for treating or preventing cancer in a patient suffering therefrom, the method comprising administering the vaccine according to claim 1 to the patient.

15. The method according to claim 14, wherein said vaccine is to be implanted and subsequently removed.

16. The method according to claim 15, wherein removal is accomplished between 2 to 7 days after implantation.

17. The method of claim 16, wherein removal is accomplished between 5 to 7 days after implantation.

* * * * *